(12) United States Patent
Westwood et al.

(10) Patent No.: US 10,407,355 B2
(45) Date of Patent: Sep. 10, 2019

(54) LIGNIN PROCESSING

(71) Applicant: UNIVERISTY COURT OF THE UNIVERSITY OF ST ANDREWS, St Andrews (GB)

(72) Inventors: Nicholas James Westwood, Fife (GB); Christopher Stuart Lancefield, Fife (GB); Fanny Tran, Fife (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 0 days.

(21) Appl. No.: 15/504,788

(22) PCT Filed: Aug. 19, 2015

(86) PCT No.: PCT/GB2015/052415
§ 371 (c)(1),
(2) Date: Feb. 17, 2017

(87) PCT Pub. No.: WO2016/027091
PCT Pub. Date: Feb. 25, 2016

(65) Prior Publication Data
US 2017/0275215 A1 Sep. 28, 2017

(30) Foreign Application Priority Data
Aug. 20, 2014 (GB) .................... 1414829.0

(51) Int. Cl.
C07B 41/06 (2006.01)
C07G 1/00 (2011.01)
D21C 11/00 (2006.01)
C07B 41/02 (2006.01)
C07C 39/10 (2006.01)

(52) U.S. Cl.
CPC .............. *C07B 41/06* (2013.01); *C07B 41/02* (2013.01); *C07C 39/10* (2013.01); *C07G 1/00* (2013.01); *D21C 11/0007* (2013.01)

(58) Field of Classification Search
CPC ........................................................ C07G 1/00
See application file for complete search history.

(56) References Cited

U.S. PATENT DOCUMENTS

| 4,602,982 | A | | 7/1986 | Samuelson | |
|---|---|---|---|---|---|
| 5,002,634 | A | * | 3/1991 | Dimmel | C07C 46/00 162/72 |
| 5,549,789 | A | * | 8/1996 | Atalla | D21C 9/1057 162/65 |
| 8,648,218 | B2 | * | 2/2014 | Liu | C07C 37/50 44/605 |
| 9,422,215 | B2 | * | 8/2016 | Samec | C07G 1/00 |
| 2008/0050792 | A1 | * | 2/2008 | Zmierczak | C10G 1/002 435/161 |
| 2010/0121110 | A1 | * | 5/2010 | Voitl | C08H 6/00 568/426 |
| 2010/0137663 | A1 | * | 6/2010 | Chen | C10G 1/002 585/252 |
| 2011/0275868 | A1 | * | 11/2011 | Prochazka | C07C 4/16 585/242 |
| 2012/0302796 | A1 | * | 11/2012 | Dhepe | C07C 37/004 568/309 |
| 2013/0060071 | A1 | * | 3/2013 | Delledonne | C07C 37/54 585/310 |
| 2013/0232853 | A1 | | 9/2013 | Peterson et al. | |
| 2014/0235838 | A1 | * | 8/2014 | Stahl | C07G 1/00 530/504 |
| 2015/0041083 | A1 | * | 2/2015 | Yoshikawa | C07G 1/00 162/19 |
| 2015/0218073 | A1 | * | 8/2015 | Samec | C07C 45/29 568/426 |
| 2015/0259261 | A1 | * | 9/2015 | Li | C05C 9/005 71/23 |
| 2015/0259368 | A1 | * | 9/2015 | Stahl | C07G 1/00 530/507 |
| 2015/0299064 | A1 | * | 10/2015 | Sharma | C07G 1/00 568/322 |
| 2015/0337214 | A1 | * | 11/2015 | Murray | C10G 3/45 585/357 |
| 2016/0130202 | A1 | * | 5/2016 | Barta | C07C 51/09 530/507 |

FOREIGN PATENT DOCUMENTS

| CN | -103508857 A | * | 1/2014 | |
|---|---|---|---|---|
| WO | 2011003029 A2 | | 1/2011 | |
| WO | WO-2014039002 A1 | * | 3/2014 | ............. C07C 45/29 |

OTHER PUBLICATIONS

Machine Translation of CN 103508857 (Year: 2017).*
Kim et al. (J. Phys. Chem. Lett. 2011, 2,2846-2852) (Year: 2011).*
Becker et al. (J. Org. Chem. 45, 1980, 1596-1600) (Year: 1980).*
Nichols et al. (J. Am. Chem. Soc. 2010, 132,12554-55) (Year: 2010).*
Christopher S. Lancefield et al., "Isolation of Functionalized Phenolic Monomers through Selective Oxidation and C-0 Bond Cleavage of the β-O-4 Linkages in Lignin" Angewandte Chemie International Edition, vol. 54, No. 1, Jan. 2, 2015, pp. 258-262.
Alireza Rahimi et al, "Formic-Acid-Induced Depolymerization of Oxidized Lignin to Aromatics", NATURE, vol. 515, No. 7526, Nov. 2, 2014, pp. 249-252.
Nikhil D. Patil et al, "Selective cleavage of the Cα-Cβ linkage in lignin model compounds via Baeyer-Villiger oxidation", Organic & Biomolecular Chemistry, vol. 13, No. 11, Jan. 1, 2015, pp. 3243-3254.

(Continued)

Primary Examiner — Liam J Heincer
(74) Attorney, Agent, or Firm — Christopher J. Knors; Moore & Van Allen PLLC

(57) ABSTRACT

A method of depolymerizing a lignin includes oxidizing the lignin to provide an oxidized lignin wherein benzylic —OH of β-O-4 linkages have been converted to carbonyl. The oxidized lignin is depolymerized with a metal selected from the group consisting of zinc, magnesium, aluminum and titanium or mixtures thereof, in the presence of an ammonium salt or carbon dioxide. Also described are methods for manufacturing phenolic products from lignin and a method for the cleavage of a β-O-4 linkage in a substrate.

25 Claims, No Drawings

(56) References Cited

OTHER PUBLICATIONS

John D. Nguyen et al, "A Photochemical Strategy for Lignin Degradation at Room Temperature", Journal of the American Chemical Society, vol. 136, No. 4, Jan. 29, 2014, pp. 1218-1221.
Joseph Zakzeski et al, "Transition metal catalyzed oxidation of Alcell lignin, soda lignin, and lignin model compounds in ionic liquids", Green Chemistry, vol. 12, No. 7, Jan. 1, 2010, pp. 1225, 1227-1228.
Fachuang Lu et al, "DFRC Method for Lignin Analysis. 1. New Method for β-Aryl Ether Cleavage: Lignin Model Studies", Journal of Agricultural and Food Chemistry, vol. 45, No. 12, Dec. 1, 1997, pp. 4655-4660.
International Search Report and Written Opinion for International Application No. PCT/GB2015/052415, dated Oct. 6, 2015, 17 pages.
Alireza Rahimi, "Chemoselective Metal-Free Aerobic Alcohol Oxidation in Lignin" Journal of the American Chemical Society, vol. 135, No. 17, Apr. 9, 2013, pp. 6415-6418.
Arjan Kloekhorst et al. "Catalytic Hydrotreatment of Pyrolytic Lignins to Give Alkylphenolics and Aromatics Using a Supported Ru Catalyst" Royal Society of Chemistry, vol. 4, 2014, 2367-2377.
UKIPO; Search Report for United Kingdom Application No. GB1414829.0 dated Feb. 23, 2015, 4 pages.
Takuya Yoshikawa et al. "Production of Phenols from Lignin via Depolymerization and Catalytic Cracking" Fuel Processing Technology, vol. 108, 2013, pp. 69-75.
Holger Werhan et al. "Acidic Oxidation of Kraft Lignin into Aromatic Monomers Catalyzed by Transition Metal Salts" Institute of Process Engineering, vol. 65, 2011, pp. 703-709.
Wu, Adam, et al; "Hydrogenolysis of β-O-4 lignin model dimers by a nuthenium-xantphos catalyst," Dalton Transactions, 2012, pp. 11093-11106, vol. 41.

\* cited by examiner

LIGNIN PROCESSING

CROSS-REFERENCE TO RELATED APPLICATIONS

This application is a 35 U.S.C. § 371 National Stage Application of International Application No. PCT/GB2015/052415, filed Aug. 19, 2015, which claims the benefit of U.K. Application No. 1414829.0 filed on Aug. 20, 2014, the entirety of each of which is incorporated herein by reference.

FIELD OF THE INVENTION

The present invention relates to the processing of lignin to provide useful small molecules.

BACKGROUND TO THE INVENTION

Technologies to produce chemicals and fuels from renewable bio-resources have been the focus of intense development as global reserves of fossil fuels fall and their prices rise. In particular lignocellulosic biomass, containing cellulose, hemicellulose and lignin, is considered an important future resource in the context of a biorefinery. Whilst technologies for the production of ethanol derived from the cellulosic component of lignocellulosic biomass are already in commercial operation, processes making use of the lignin component are still limited. This constitutes a significant drawback in biorefineries where the valorization of all components of the biomass is necessary for economic viability. In addition, despite lignin being a major by-product of the pulp and paper industry, only 2% of the lignin currently produced is used commercially. The valorization of lignin has therefore become an important challenge that has yet to be solved.

Lignin constitutes between 15-30% of the biomass and up to 40% of the energy content of most higher plants. The heterogeneous nature of lignin means that the ratio of monomers and structural units depends highly on the plant source and the extraction process. However the major structural unit is, in almost all lignins, the β-O-4 (β-aryl ether) linkage with lower amounts of β-β (resinol), β-5 (phenylcourmaran), β-1 (1,2-diarylpropane), 5-5 (biphenyl) and 4-O-5 (diaryl ether) linkages. A schematic view of a lignin polymeric structure and illustration of the various types of linkage between aromatic moieties is provided in Scheme 1, below. Sinapyl alcohol derived and coniferyl alcohol derived units may be designated S and G respectively.

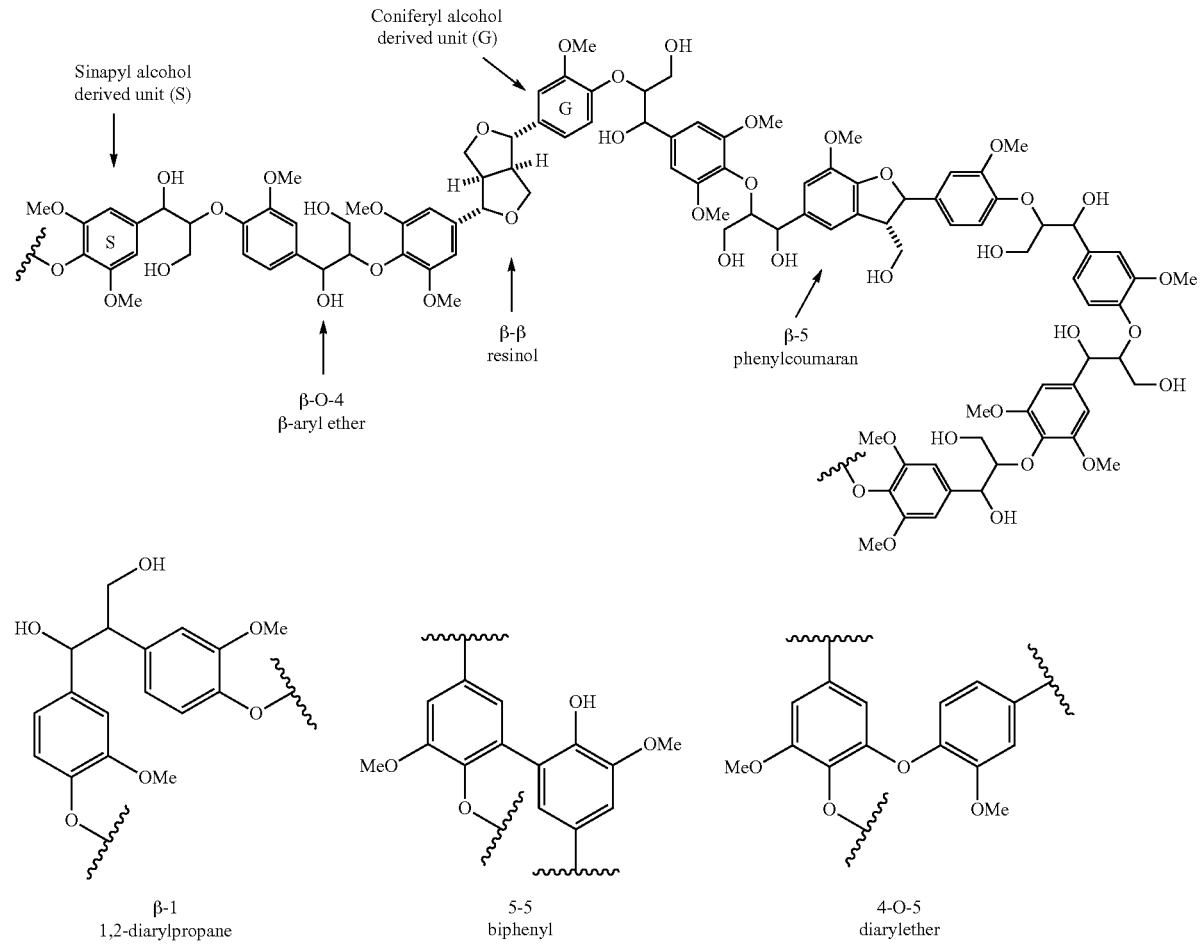

Scheme 1

The major hurdle to lignin utilisation for the production of biorenewable chemicals is the selective depolymerisation of this recalcitrant material to monomers. It is for this reason that new chemical processes are needed. Several approaches have been suggested. Recently, the selective oxidation of lignin combined with a second chemical treatment has been suggested as a method to bring about the selective depolymerisation of lignin. Rahimi et al (Ref 1), show oxidation of lignin model compounds with molecular oxygen in the presence nitric and hydrochloric acids and 4-acetamido-TEMPO, followed by a second step of cleavage at C—C bonds with hydrogen peroxide under basic conditions. They suggest the possible application to lignins. Nguyen et al (Ref 2) propose a two-step process, also demonstrated only on model compounds, where an oxidation with Bobbitt's salt ([4-AcNH-TEMPO]$BF_4$) is the first step. This can be followed as a second step with a cleavage of C—O bonds using an amine hydrogen donor and formic acid in the presence of an iridium complex and light.

There remains the need to find new approaches to obtaining useful substances from lignin.

DESCRIPTION OF THE INVENTION

According to a first aspect the present invention provides a method of depolymerising a lignin, the method comprising:
oxidising the lignin to provide an oxidised lignin wherein benzylic —OH of β-O-4 linkages have been converted to carbonyl; and
depolymerising the oxidised lignin with a metal selected from the group consisting of zinc, magnesium, aluminium, titanium and mixtures thereof, in the presence of an ammonium salt or carbon dioxide.

The oxidising agent for the lignin may comprise molecular oxygen, a quinone and a source of nitrogen dioxide. Alternatively the oxidising agent for the lignin may comprise a quinone. Oxidation with quinone reagents has been found to produce an oxidised lignin where at least some of the β-O-aryl moieties (β-O-4 linkages) have the benzylic —OH converted to carbonyl.

Other reagents which carry out the same conversion of the β-O-4 linkages may be employed for the oxidising step of the method. For example 2,2,6,6-Tetramethylpiperidin-1-yl) oxy (TEMPO) and its derivatives. For example, 4-hydroxy-TEMP, 4-acetamido-TEMPO and other nitroxyl radicals such as 2-azaadamantane N-oxyl (AZADO) or 9-azanoradamantane N-oxyl. Other reagents such as Pd/C or a vanadium catalyst may also be appropriate to carry out this oxidation.

Any lignin including β-O-4 linkages may be employed in the process. Depending on the extraction conditions typical β-O-4 linkage levels may be of the order of ~45-65% of the total linkages in the lignin.

The oxidising and the depolymerisation steps may be carried out as separate process steps. If so the oxidised lignin may be isolated from the initial reaction mixture and then subjected to the depolymerising step.

Alternatively and conveniently the method may be carried out as a one pot process, with both the oxidation and depolymerisation steps carried out one after the other. A convenient one pot process has been shown to operate successfully where the oxidising step employs molecular oxygen in the presence of a quinone and a source of nitrogen dioxide, or with a quinone as oxidant.

The oxidation step may be carried out with 2,3-dichloro-5,6-dicyano-1,4-benzoquinone (DDQ), Other quinones that may be used include p-chloroanil, o-chloroanil, benzoquinone, 2-chloroanthroquinone, and 1,4,5,8-tetrachloroanthroquinone. The oxidising step with a quinone has been found to oxidise at least β-O-aryl linkages of lignin. The oxidising step may be carried out using an approximately equal weight of the oxidant quinone to the lignin, or more.

Alternatively and conveniently use is made of molecular oxygen in combination with a quinone (e.g. DDQ) and a source of nitrogen dioxide ($NO_2$) such as an alkyl nitrite, for example tert-butyl nitrite. Other sources of nitrogen dioxide can include $NO_2$ itself, nitrite salts such as $NaNO_2$, nitric acid/hydrochloric acid mixtures or nitric oxide (NO) which is commercially available. With such an oxidising system the quinone, such as DDQ can be utilised in a catalytic fashion. For example, at an amount of 2 to 30% by weight of lignin or even 5-20% by weight of lignin. The proportion of benzylic —OH converted to carbonyl in the β-O-4 linkages using such systems can be high, for example up to 100% as determined by 2D NMR tracking of the appearance of cross peaks for oxidised structures in the lignin and the disappearance of the cross peaks for the original β-O-4 linkages. More generally, oxidation involving a quinone, or molecular oxygen in the presence of a quinone and a source of nitrogen dioxide, can oxidise a lignin at the β-O-4 linkages to an extent of 40% or more as determined by such 2D NMR tracking measurements.

The oxidising step is conveniently carried out in an alcoholic solvent (a solvent containing at least one hydroxyl function) or solvent mixture. Water is also a suitable solvent. Suitable solvents include water, methanol, ethanol, glycerol and mixtures thereof. Glycol ether solvents are convenient, for example 2-methoxyethanol.

Co-solvents may be employed to improve conversion to the oxidised product. Co-solvents may include alkyl nitriles such as acetonitrile, carboxylic acids such as acetic acid, aromatic solvents such as substituted benzenes. For example, halo aromatics (e.g. chlorobenzene). Advantageously an alkyl ether, for example dialkyl ethers of ethylene glycol or propylene glycol such as 1,2-dimethoxyethane are employed. Other alkyl ethers such as 1,2-diethoxyethane, or cyclopentyl methyl ether may be employed. Mixtures of these solvents may be employed together with an alcoholic solvent system that may include water.

The oxidation step; when molecular oxygen in the presence of a quinone and a source of nitrogen dioxide, or a quinone, is employed may conveniently be run at ambient or elevated temperature, for example at 20-130° C. or even 60-110° C. Typically the reaction may be run at about 80° C., say from 70 to 90° C. Oxygen may be supplied at atmospheric pressure above the reaction mixture. Mixing may be improved by bubbling oxygen through the reaction mixture. Where bubbling oxygen through the reaction mixture is employed it is preferred that the gaseous atmosphere should be recycled to avoid loss of the co-oxidant $NO_2$ from the system. The reaction may be carried out under an elevated pressure to aid oxygen usage.

If desired the oxidised lignin may be isolated before the depolymerisation step is carried out. For example, by precipitation from an alcohol containing solvent system by addition of an anti-solvent such as diethyl ether or cyclopentyl methyl ether; alternatively by evaporation of some or all of the solvent employed.

An oxidised lignin, where at least some of the β-O-aryl moieties (β-O-4 linkages) have the benzylic —OH converted to carbonyl is employed for the depolymerisation step. Thus according to a second aspect the present invention provides a method of depolymerising an oxidised lignin wherein benzylic —OH of β-O-4 linkages have been converted to carbonyl, the method comprising:
reacting the oxidised lignin with a metal selected form the group consisting of zinc, magnesium, aluminium and titanium or mixtures thereof, in the presence of an ammonium salt or carbon dioxide.

For a depolymerisation according to either the first or second aspects of the invention, the following conditions may be employed.

The ammonium salt may be ammonium chloride for example. The metal may be in powder form. Zinc may be preferred on cost grounds. An activated form of zinc, such as a zinc-copper couple may be employed. The presence of an ammonium salt or $CO_2$ may not be required when an activated zinc is employed. Alternative ammonium salts include ammonium formate, ammonium acetate, ammonium sulphate and ammonium bisulphate.

As a yet further alternative an acid or mixture of acids e.g. a mineral acid or an organic acid, may be employed to activate the metal for the depolymerisation step. Suitable mineral acids for this duty can include hydrochloric and sulphuric acids and mixtures thereof. Suitable organic acids for this duty can include carboxylic acids such as formic and acetic acid and mixtures thereof.

The oxidised lignin may be reacted to depolymerise in an aqueous alcoholic solvent system, for example a water/glycol ether system such as water and 2-methoxyethanol mixtures. Co-solvents may be present and may include alkyl nitriles such as acetonitrile, carboxylic acids such as acetic acid, aromatic solvents such as substituted benzenes. For example, halo aromatics (e.g. chlorobenzene). Advantageously an alkyl ether, for example dialkyl ethers of ethylene glycol or propylene glycol such as 1,2-dimethoxyethane are employed. Other alkyl ethers such as 1,2-diethoxyethane, or cyclopentyl methyl ether may be employed. Mixtures of these solvents may be employed together with an alcoholic solvent that optionally includes water or mixture of alcoholic solvents that optionally includes water.

Mixtures of from 9:1 to 7:3 of 2-methoxyethanol:water (by volume) may be employed, for example a mixture of 8:2 of 2-methoxyethanol:water (by volume). Such solvent systems have been found to be good solvents for oxidised lignins. As an alternative mixtures of 2-methoxyethanol and 1,2-dimethoxyethane, optionally also including water, may be employed. 2-methoxyethanol:1,2-dimethoxyethane in a range of proportions of from 1:0-1:2 by volume may be employed, for example of from 1:0-1:1. Water may be used in the range of from 0-50% of the total volume of the reaction solvent.

The depolymerisation step may conveniently be run at ambient or elevated temperature, for example at 20-120° C. or even 60-110° C. Typically the reaction may be run at about 80° C., say from 70 to 90° C. The reaction may be run at atmospheric or elevated pressure.

After completion of the depolymerisation reaction, unreacted metal may be filtered off for reuse or disposal.

Depolymerised products may then be obtained from the reaction mixture. Conveniently addition of water or addition to water is used to precipitate solids, a lignin fraction that has not been converted into low molecular weight products. The lignin fraction can be filtered off and washed with solvent to extract low molecular weight products. Similarly the filtrate may be extracted with solvent to extract low molecular weight products. The low molecular weight products may then be obtained from the combined extraction solvent layers by any suitable technique, for example evaporation of the solvent followed by chromatography of the residue (for example on silica) to provide purified compounds. Suitable solvents for extraction purposes include ethyl acetate tert-butyl methyl ether and cyclopentyl methyl ether.

As an alternative to carrying out the process of the first aspect of the invention as two separate steps, oxidation to an oxidised lignin, followed by depolymerisation of an oxidised lignin, the process may be carried out as a "one pot" process. Following the oxidation step water is added to the reaction mixture including oxidised lignin in an alcoholic solvent system. For example 20% water by volume of the original solvent is added to a reaction mixture using a glycol ether (e.g. 2-methoxyethanol) based solvent system. The depolymerisation step is then carried out as discussed above.

The lignin fraction left at the end of the process may be utilised for energy generation, carbon fibre production or may be further processed to obtain useful products. For example as a substrate for a further catalytic degradation to provide further small molecule products. For example it may be subject to thermal depolymerisation to produce a pyrolytic lignin for use as a fuel source and/or for further treatment to provide useful organic chemicals (Ref 3).

The depolymerisation of the oxidised lignin has been found to produce phenolic products, including compounds of formulas I, II and III:

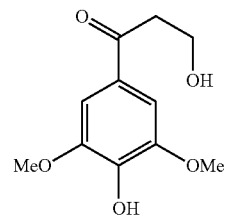 [SMILES: COc1cc(C(=O)CCO)cc(OC)c1O]

I

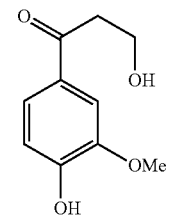 [SMILES: COc1cc(C(=O)CCO)ccc1O]

II

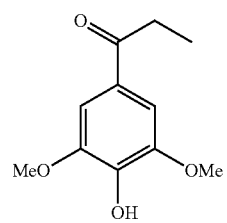

III

I is 3-Hydroxy-1-(4-hydroxy-3,5-dimethoxyphenyl)propan-1-one;

II is 3-Hydroxy-1-(4-hydroxy-3-methoxyphenyl)propan-1-one; and

III is 1-(4-Hydroxy-3,5-dimethoxyphenyl)propan-1-one.

The oxidation of the lignin followed by depolymerisation is illustrated in Scheme 2 below which shows oxidation of benzylic hydroxyls (A) of a portion of a lignin structure to the corresponding carbonyls (B). This is followed by zinc mediated depolymerisation involving cleavage at phenolic ether linkages (C—O) to provide phenolic monomers such as I.

Scheme 2

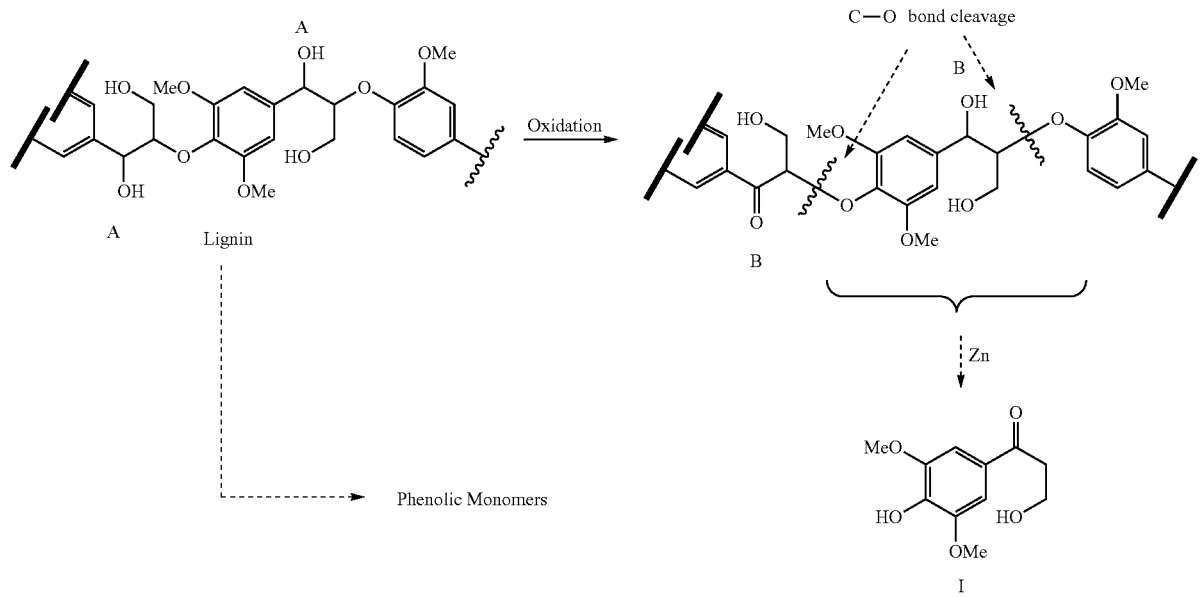

The phenolic products can find use as intermediates for manufacture of useful organic chemicals.

Thus in a third aspect the present invention provides a method of manufacture of a phenolic product of general formula Z:

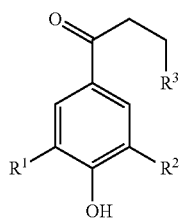

wherein $R^1$ and $R^2$ are, independently for each occurrence, —H or —OMe and $R^3$ is —H or —OH;
  wherein the method comprises oxidising a lignin to an oxidised lignin wherein benzylic —OH of the β-O-4 linkages have been converted to carbonyl; and
  depolymerising the oxidised lignin with a metal selected from the group consisting of zinc, magnesium, aluminium, titanium and mixtures thereof, in the presence of an ammonium salt or carbon dioxide.

The method may be employed to prepare at least one of the compounds according to formula I, II or III, as shown above, or any mixture of these.

The method of the third aspect may be carried out using the solvents and conditions suggested above with respect to the first and second aspects of the invention.

Isolation of the phenolic product or products (e.g. of formula I, II or III) may be carried out in the same way as described for the first and second aspects of the invention. Thus after completion of reaction, unreacted metal may be filtered off for reuse or disposal.

Conveniently addition of water to the reaction mixture is used to precipitate solids, a lignin fraction that has not been converted into the phenolic products. The lignin fraction can be filtered off and washed with solvent to extract low molecular weight phenolic products. Similarly the filtrate may be extracted with solvent to extract low molecular weight phenolic products. The phenolic products may then be obtained from the combined extraction solvent layers by any suitable technique, for example evaporation of the solvent followed by chromatography of the residue (for example on silica) to provide purified compounds. Suitable solvents for extraction purposes include ethyl acetate. Chromatography on silica may use solvent systems such as petroleum ether:ethyl acetate (0 to 55% by volume).

According to a fourth aspect the present invention provides a method for the cleavage of a β-O-4 linkage in a substrate, the method comprising:
  oxidising the β-O-4 linkage to provide an oxidised product wherein benzylic —OH of β-O-4 linkages have been converted to carbonyl; and
  depolymerising the oxidised lignin with a metal selected from the group consisting of zinc, magnesium, aluminium, titanium and mixtures thereof, in the presence of an ammonium salt or carbon dioxide.

The method of the fourth aspect may be carried out using the solvents and conditions suggested above with respect to the first and second aspects of the invention.

DESCRIPTION OF SOME PREFERRED EMBODIMENTS AND EXPERIMENTAL RESULTS MODEL COMPOUND STUDIES

Methoxy substituted β-O-4 linked diaryl compounds (1a to 1d) and veratryl alcohol (1e) were subjected to an oxidation procedure using DDQ, $^t$BuONO and $O_2$ as the oxidising system and 2-methoxyethanol as solvent. Oxidised products 2a to 2e were obtained in high yields as indicated beside each entry in Table 1 below, which highlights the selectivity and reactivity of the catalytic oxidation conditions employed.

TABLE 1
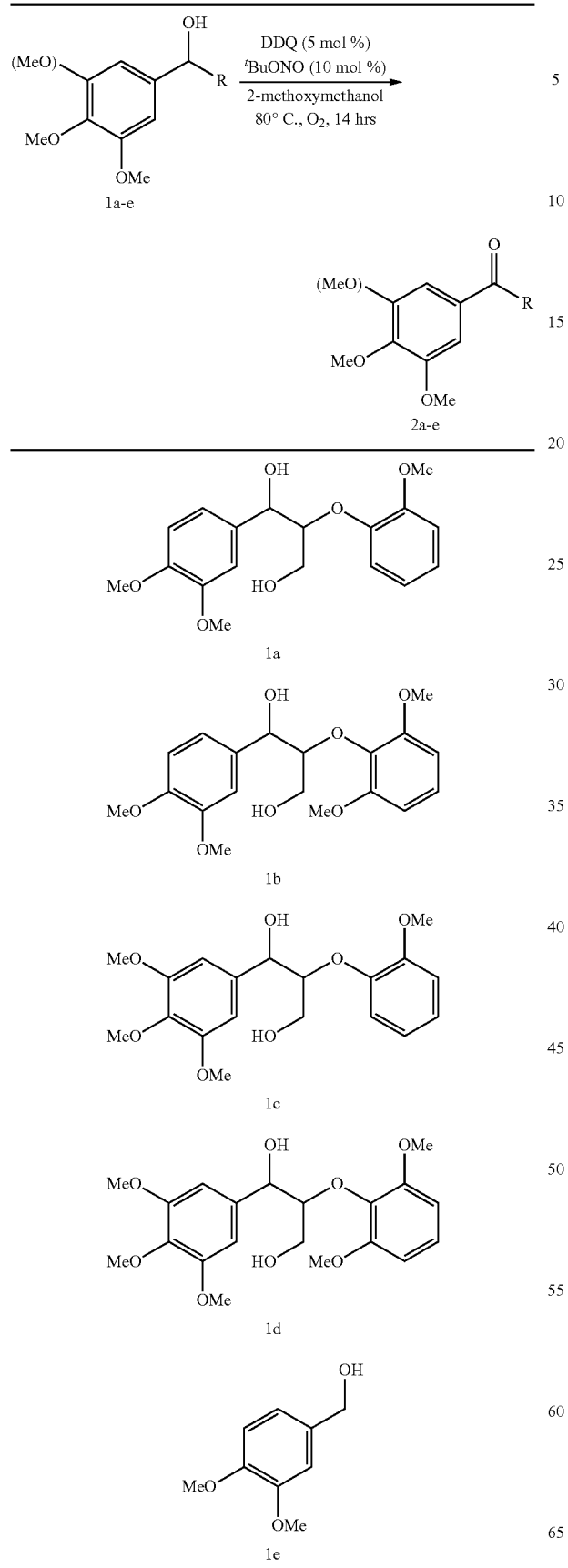
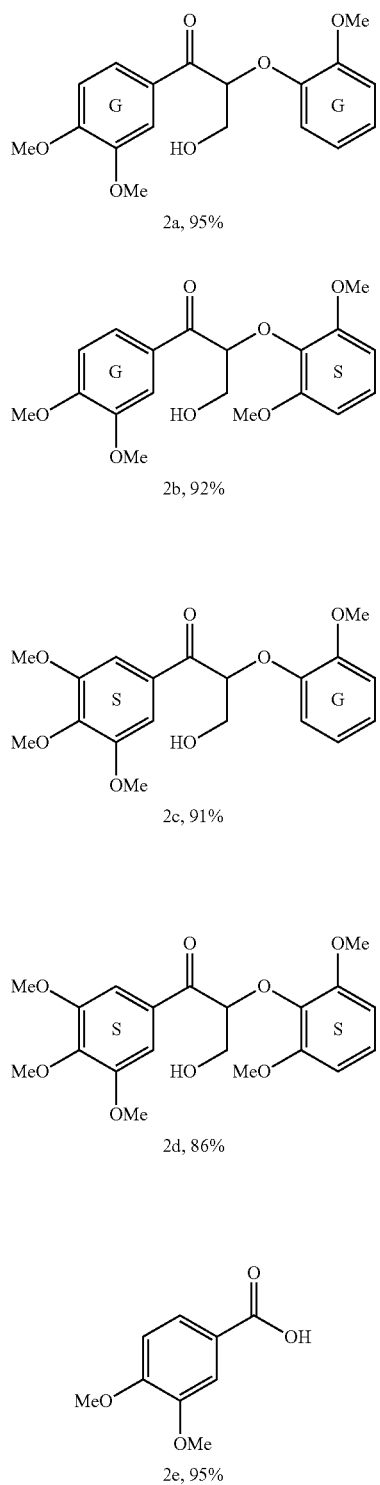
Model Polymer Studies
A polymer incorporating equal proportions of both S and G units was prepared as a model for a β-O-4 rich hardwood lignin and the results of the oxidation experiments assessed using semi-quantitative 2D-HSQC NMR experiments.

The polymer was prepared according to the following reaction (Scheme 3)

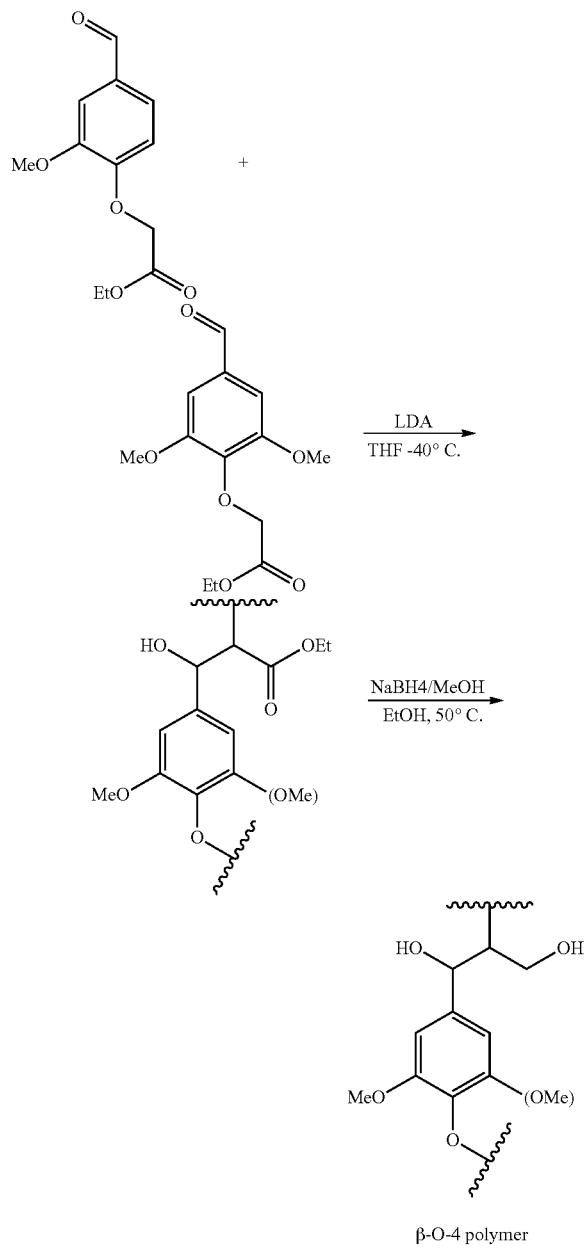

β-O-4 polymer

The polymer was initially treated under identical conditions to those used for the monomer studies (Table 2 below, Entry 1). The outcome of the reaction indicated that whilst the catalytic oxidation still proceeded, the conversion was lower than seen in the monomer series where close to complete conversion was achieved. As a result further optimisation of the reaction conditions was sought. Increasing the DDQ loading to 10 mol % improved conversions significantly (Entry 2). It was additionally found that the addition of 1,2-dimethoxyethane as a non-protic co-solvent markedly improved conversions (Entries 3 and 4). At 10 mol % DDQ and 10 mol % $^t$BuONO oxidation reached 91%. However, to achieve almost complete oxidation the loading of DDQ and $^t$BuONO was increased to 20 mol % (Entry 6). The beneficial effect of the co-solvent in this reaction may in part, be explained by an increase in the effective lifetime of DDQ under these conditions. It is interesting to note that G units appear significantly easier to oxidise than the S units. This observation is consistent with the reaction proceeding through the formation of a benzyl cation intermediate which is resonance stabilised by the para-methoxy substituent but destabilised by the meta-methoxy substituents through inductive electron withdrawal. This means the G unit, which is substituted with only one meta-methoxy group, is easier to oxidise than the S unit bearing two meta-methoxy groups.

TABLE 2 model polymer
S:G = 1:1 oxidised model polymer

| Entry | DDQ (mol %) | tBuONO (mol %) | Solvent System[a] | Conversion (%)[b] Total | G | S |
|---|---|---|---|---|---|---|
| 1 | 5 | 10 | A | 50 | 64 | 35 |
| 2 | 10 | 10 | A | 74 | 83 | 64 |
| 3 | 5 | 10 | B | 69 | 81 | 57 |
| 4 | 10 | 10 | B | 91 | 100 | 82 |
| 5 | 15 | 15 | B | 97 | 100 | 94 |
| 6 | 20 | 20 | B | 99 | 100 | 98 |

[a]A = 2-methoxyethanol, B = 2-methoxyethanol/1,2-dimethoxyethane (2:3) [b]Conversions were determined by integration of the aromatic cross peaks characteristic of oxidised and unoxidised structures in the 2D HSQC NMR. Error analysis indicated the standard deviation for these measurements was less than <0.05.

Lignin Experiments

In experiments using actual lignin as a substrate described below, a typical dioxasolv process was used to extract lignin from Birch sawdust (*Betula pendula*). Birch sawdust is heated to reflux for 1 hour in a 8:2 mixture of dioxane and 2M aq. HCl using 1:8 mass:volume ratio. The liquor containing the lignin is then separated by filtration, partially concentrated under reduced pressure and precipitated in water. The precipitated lignin is then collected by filtration, dissolved in dioxane/water 9:1 and purified by precipitation with diethyl ether. The isolated lignin was syringyl rich and contained a high proportion of β-O-4 linkages, smaller amounts of β-β (resinol) and only just detectable amounts of the β-5 linkage (Scheme 1). Oxidation under catalytic DDQ conditions proceeded smoothly to give an oxidised lignin in which the appearance of the desired alpha ketone β-O-4 structure could be readily identified in the 2D HSQC NMR spectrum. Concurrent to the appearance of the cross peaks assigned to the alpha ketone structure, complete disappearance of the cross peaks assigned to the unoxidised β-O-4 structure was observed. The Integration relative to the sum of the aromatic region suggested that the selectivity seen in model studies was maintained in lignin itself as the relative volume integrals of the β-O-4 cross peaks before and after oxidation are almost identical (22.0 protons and 23.4 protons per 100 aromatic protons respectively).

General Procedure for Lignin Oxidations:

To a solution of lignin in 2-methoxyethanol (14 mL/g) or 2-methoxyethanol/1,2-dimethoxyethane (DME) (2:3, 14 mL/g) was added DDQ followed by ʹBuONO. The reaction mixture was placed under an $O_2$ atmosphere (balloon) and stirred at 80° C. for 14 hrs. The oxidised lignin was isolated by precipitation in 10 volumes of $Et_2O$ and filtering, alternatively the lignin solution was used in the next step without any further processing.

Results of experiments are given in the table below.

| Entry | DDQ (wt %) | ʹBuONO (mol %) | Solvent | Degree of oxidation (%)[a] |
|---|---|---|---|---|
| 1 | 5 | 10 | 2-methoxyethanol/DME | 46 |
| 2 | 10 | 10 | 2-methoxyethanol/DME | 77 |
| 3 | 10 | 20 | 2-methoxyethanol/DME | 78 |
| 4 | 10 | 20 | 2-methoxyethanol | 66 |

[a]as determined by the relative integration of $S_{2,6}$ and $S'_{2,6}$ aromatic cross peaks in the NMR spectrum corresponding to the syringyl rings before and after oxidation. The regions corresponding to the syringyl units in lignin before and after oxidation are well resolved and so this comparison is used as a measure of oxidation.

Zinc Mediated Depolymerisation of Lignin:

From Isolated Oxidised Lignin:

To a solution of lignin (600 mg) in 2-methoxyethanol (8.4 mL) was added water (2.1 mL) followed by $NH_4Cl$ (740 mg) and zinc dust (900 mg). The reaction mixture was heated at 80° C. for 1 hour, cooled and filtered to remove excess zinc. The reaction mixture was then added to water (30 mL), acidified to pH 1 by the addition of 1M HCl which causes the lignin to flocculate and then the mixture was filtered. The residual lignin was washed with EtOAc and the aqueous filtrate extracted with EtOAc (5×20 mL). The organic extracts and washings were combined, washed with sat. $NaHCO_3$, brine, dried ($MgSO_4$) and concentrated in vacuo. The crude extract was purified by column chromatography petroleum ether:ethyl acetate (0 to 55%) to yield 3 products. II (3.5 mg, 0.58 wt %), I (29 mg, 5 wt %) and III (3.4 mg, 5.7 wt %).

One Pot Procedure:

Lignin (2.40 g) was treated according to the general procedure for catalytic oxidation in 2-methoxyethanol/1,2-dimethoxyethane. After the reaction time water (7 mL) was added followed by $NH_4Cl$ (3.0 g) and zinc dust (3.60 g). The mixture was then heated at 80° C. for 1 hr, cooled and filtered to remove excess zinc. The reaction mixture was then added to water (100 mL), acidified to pH 1 by the addition of 1M HCl which causes the lignin to flocculate and then the mixture was filtered. The residual lignin was washed with EtOAc and the aqueous filtrate extracted with EtOAc (5×50 mL). The organic extracts and washings were combined, washed with sat. $NaHCO_3$, brine, dried (over $MgSO_4$) and concentrated in vacuo. The crude extract was purified by column chromatography on silica with petroleum ether:ethyl acetate (0 to 55%) to yield 3 products. II (11 mg, 0.46 wt %), I (110 mg, 4.6 wt %) and III (12 mg, 0.50 wt %).

Isolated Products:

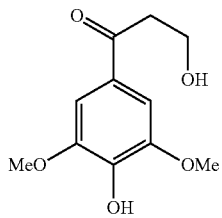

3-Hydroxy-1-(4-hydroxy-3,5-dimethoxyphenyl)propan-1-one (I)

White solid. M.p. 109-110° C. Spectral data are consistent with those reported in the literature.

$^1$H NMR (400 MHz, $CDCl_3$) δ=7.25 (s, 2H), 6.08 (s, 1H), 4.03 (t, J=5.4, 2H), 3.95 (s, 6H), 3.19 (t, J=5.4, 2H), 2.74 (s, 1H).

$^{13}$C NMR (101 MHz, $CDCl_3$) δ199.00, 147.0, 140.3, 128.4, 105.6, 58.4, 56.6 (2C), 40.0.

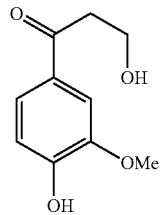

3-Hydroxy-1-(4-hydroxy-3-methoxyphenyl)propan-1-one (II)

Pale yellow amorphous solid. Spectral data are consistent with those reported in the literature.

$^1$H NMR (500 MHz, $CDCl_3$) δ=7.58-7.50 (m, 2H), 6.95 (d, J=8.1, 1H), 6.17 (s, 1H), 4.02 (t, J=5.3, 2H), 3.96 (s, 3H), 3.19 (t, J=5.3, 2H), 2.78 (s, 1H).

$^{13}$C NMR (126 MHz, $CDCl_3$) δ=199.2, 150.9, 146.8, 129.8, 123.8, 114.1, 109.7, 58.5, 56.2, 39.9.

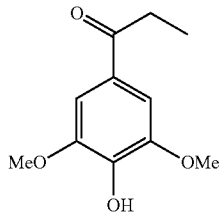

1-(4-Hydroxy-3,5-dimethoxyphenyl)propan-1-one (III)

Colourless solid. M.p. 102-104° C. (lit. 109-111° C.). Spectral data are consistent with those reported in the literature.

$^1$H NMR (400 MHz, $CDCl_3$) δ=7.27 (s, 2H), 5.92 (s, 1H), 3.96 (s, 6H), 2.97 (q, J=7.3, 2H), 1.23 (t, J=7.3, 3H).

$^{13}$C NMR (101 MHz, $CDCl_3$) δ=199.4, 146.9, 139.6, 128.7, 105.5 (2C), 56.6 (2C), 31.5, 8.7.

REFERENCES

1) A. Rahimi, A. Azarpira, H. Kim, J. Ralph, S. S. Stahl, J. Am. Chem. Soc. 2013, 135, 6415-6418;
2) J. D. Nguyen, B. S. Matsuura, C. R. J. Stephenson, J. Am. Chem. Soc. 2013, 136, 1218-1221.
3) A. Kloekhorst, J. Wildschut, H. J. Heeres, Catal. Sci. Technol., 2014, 4, 2367-2377.

The invention claimed is:

1. A method of depolymerizing a lignin, the method comprising:
    oxidizing benzylic OH of β-O-4 linkages of a lignin with molecular oxygen in the presence of a quinone and a source of nitrogen dioxide to provide an oxidized lignin wherein the benzylic OH of β-O-4 linkages have been converted to carbonyl; and
    depolymerizing the oxidized lignin with a metal selected from the group consisting of zinc, magnesium, aluminum and titanium or mixtures thereof, in the presence of an ammonium salt or carbon dioxide, and
    producing at least one phenol according to any one of formulas I, II, or III:

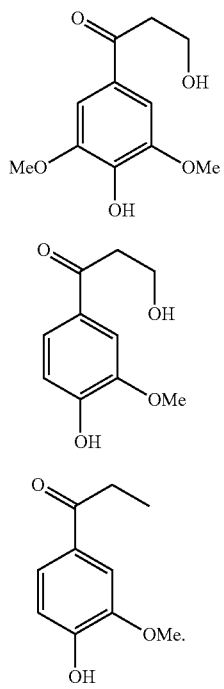

2. The method of claim 1, wherein the process is carried out as a one pot process, with both the oxidation and depolymerization steps carried out one after the other.

3. The method of claim 1, wherein the quinone is selected from the group consisting of: 2,3-dichloro-5,6-dicyano-1,4-benzoquinone (DDQ), p-chloroanil, o-chloroanil, benzoquinone, 2-chloroanthroquinone, and 1,4,5,8-tetrachloroanthroquinone.

4. The method of claim 1, wherein the source of nitrogen dioxide is selected from the group consisting of: alkyl nitrites, nitrogen dioxide ($NO_2$), nitrite salts, nitric acid/hydrochloric acid mixtures and nitric oxide (NO).

5. The method of claim 1, wherein the quinone is employed at an amount of from 2 to 30% by weight of the lignin.

6. The method of claim 5, wherein the quinone is employed at an amount of from 5 to 20% by weight of the lignin.

7. The method of claim 1, wherein the oxidizing step is carried out in an alcoholic solvent or mixture comprising an alcoholic solvent.

8. The method of claim 7, wherein the oxidizing step is carried out in the presence of a co-solvent selected from the group consisting of: alkyl ethers, alkyl nitriles, carboxylic acids and aromatic solvents.

9. The method of claim 7, wherein the oxidizing step is carried out in a solvent system comprising 2-methoxyethanol, a mixture of 2-methoxyethanol and 1,2-dimethoxyethane, or a mixture of 2-methoxyethanol, 1,2-dimethoxyethane and water.

10. The method of claim 1, wherein the oxidizing step is carried out in a solvent selected from the group consisting of: water, methanol, ethanol, glycerol, glycol ethers and mixtures thereof.

11. The method of claim 1, wherein the oxidizing step is carried out at a temperature of from 20° C. to 130° C.

12. The method of claim 1, wherein an ammonium salt is employed in the depolymerization of the oxidized lignin.

13. The method of claim 12, wherein the ammonium salt is selected from the group consisting of ammonium chloride, ammonium formate, ammonium acetate, ammonium sulphate and ammonium bisulphate.

14. The method of claim 1, wherein zinc is employed as the metal in the depolymerization of the oxidized lignin.

15. The method of claim 1, wherein in the depolymerization of the oxidized lignin is carried out in a solvent comprising water and an alcohol.

16. The method of claim 15, wherein in the depolymerization of the oxidized lignin is carried out in a solvent comprising water and glycol ether.

17. The method of claim 16, wherein in the depolymerization of the oxidized lignin is carried out in a solvent comprising water and 2-methoxyethanol.

18. The method of claim 17, wherein the depolymerization of the oxidized lignin is carried out in a water and 2-methoxyethanol mixture in a ratio of from 9:1 to 7:3 of 2-methoxyethanol:water, by volume.

19. The method of claim 15, wherein the depolymerization of the oxidized lignin is carried out in the presence of a co-solvent selected from the group consisting of: alkyl ethers, alkyl nitriles, carboxylic acids and aromatic solvents.

20. The method of claim 1, wherein in the depolymerization of the oxidized lignin is carried out at from 20° C. to 120° C.

21. A method of depolymerizing an oxidized lignin, the method comprising:
    reacting an oxidized lignin, wherein benzylic —OH of β-O-4 linkages of the oxidized lignin have been converted to carbonyl, with a metal selected form the group consisting of zinc, magnesium, aluminum and titanium or mixtures thereof, in the presence of an ammonium salt or carbon dioxide;
    depolymerizing the oxidized lignin; and
    producing at least one phenol according to any one of formulas I, II, or III:

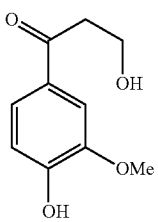

I

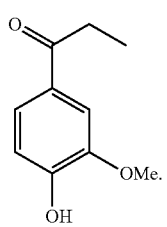

II

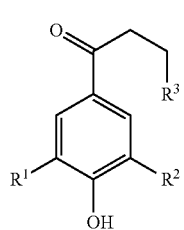

III

22. A method of manufacture of a phenolic product of general formula Z:

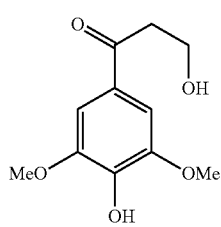

Z wherein $R^1$ and $R^2$ are, independently for each occurrence, —H or —OMe and $R^3$ is —H or —OH; wherein the method comprises oxidizing a lignin to an oxidized lignin wherein benzylic —OH of the β-O-4 linkages have been converted to carbonyl; and depolymerizing the oxidized lignin with a metal selected from the group consisting of zinc, magnesium, aluminum, titanium and mixtures thereof, in the presence of an ammonium salt or carbon dioxide.

23. The method of claim 22, wherein the phenolic product of formula Z is at least one of formulas I, II, or III:

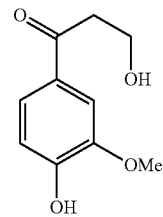

I

II

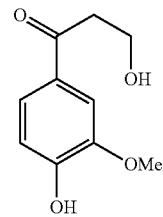

III

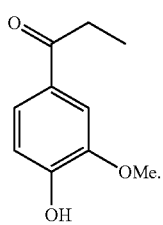

24. A method for the cleavage of a β-O-4 linkage in a substrate, the method comprising:

oxidizing a β-O-4 linkage of the substrate to provide an oxidized product wherein benzylic —OH of the β-O-4 linkage is converted to carbonyl; and depolymerizing the oxidized product with a metal selected from the group consisting of zinc, magnesium, aluminum, titanium and mixtures thereof, in the presence of an ammonium salt or carbon dioxide to produce at least one phenol according to any one of formulas I, II, or III:

I

II

III

25. A method of producing at least one phenol according to any one of formulas I, II, or III:

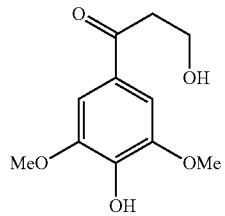
I

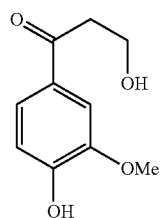
II

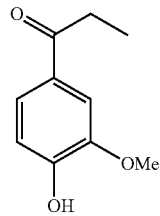
III the method comprising:
oxidatively converting benzylic —OH of β-O-4 linkages of a lignin to carbonyl with molecular oxygen in the presence of a quinone and a source of nitrogen dioxide to provide an oxidized lignin; and
reacting the oxidized lignin with a metal selected from the group consisting of zinc, magnesium, aluminum and titanium or mixtures thereof, in the presence of an ammonium salt or carbon dioxide; and
cleaving a phenolic ether linkage adjacent the carbonyl.

* * * * *